US006273882B1

(12) United States Patent
Whittier et al.

(10) Patent No.: US 6,273,882 B1
(45) Date of Patent: Aug. 14, 2001

(54) SNAP HANDLE ASSEMBLY FOR AN ENDOSCOPIC INSTRUMENT

(75) Inventors: John Whittier, Miami; Peter K. Kratsch, Sunrise, both of FL (US)

(73) Assignee: Scimed Life Systems, Maple Grove, MN (US)

(*) Notice: Subject to any disclaimer, the term of this patent is extended or adjusted under 35 U.S.C. 154(b) by 0 days.

(21) Appl. No.: 09/099,423

(22) Filed: Jun. 18, 1998

(51) Int. Cl.[7] ..................... A61B 17/00
(52) U.S. Cl. ..................... 606/1; 606/207
(58) Field of Search ..................... 606/1, 205, 207, 606/170

(56) References Cited

U.S. PATENT DOCUMENTS

| | | | | |
|---|---|---|---|---|
| 2,113,246 | | 4/1938 | Wappler . | |
| 4,763,668 | * | 8/1988 | Macek et al. | 128/751 |
| 5,147,380 | | 9/1992 | Hernandez et al. . | |
| 5,293,878 | * | 3/1994 | Bales et al. | 128/751 |
| 5,439,478 | | 8/1995 | Palmer . | |
| 5,454,378 | * | 10/1995 | Palmer et al. | 128/751 |
| 5,632,764 | * | 5/1997 | Beideman et al. | 606/205 |
| 5,741,286 | * | 4/1998 | Recuset | 606/170 |
| 5,810,876 | | 9/1998 | Kelleher . | |
| 5,967,997 | * | 10/1999 | Turturro et al. | 600/567 |

FOREIGN PATENT DOCUMENTS

| | | |
|---|---|---|
| 0 830 843 | 3/1998 | (EP) . |
| 94/22377 | 10/1994 | (WO) . |

* cited by examiner

*Primary Examiner*—Linda C. M. Dvorak
*Assistant Examiner*—Jocelyn Debra Ram
(74) *Attorney, Agent, or Firm*—Finnegan, Henderson, Farabow, Garrett & Dunner, L.L.P.

(57) ABSTRACT

An endoscopic instrument having an end effector assembly at a distal end, a flexible member connected to and extending from the end effector assembly and a handle assembly connected to the flexible member. The handle assembly includes a handle member, a nose member and a biasing element. The handle member has an inner bore. The hollow nose member has a shank configured for insertion into the inner bore. The biasing element is located within the inner bore and biases the flexible member relative to the handle member. The handle member may have a keyway or a projection configured for insertion into a keyway, and the nose member may have the other of the keyway or the projection. The flexible member has a retaining element affixed to its proximal end. The flexible member is inserted through the nose member with the retaining element located proximate the proximal end of the nose member and thereby retained between the handle member and the nose member. Relative axial movement between the handle member and the flexible member is minimized.

31 Claims, 14 Drawing Sheets

SNAP HANDLE ASSEMBLY FOR AN ENDOSCOPIC INSTRUMENT

BACKGROUND OF THE INVENTION

1. Field of the Invention

The present invention relates generally to an apparatus for attaching a control conduit to a surgical instrument. More particularly, this invention relates to a spring-biased snap assembly for attaching a flexible control conduit to a proximal handle assembly of an endoscopic biopsy instrument.

2. Description of the Related Art

Endoscopic biopsy procedures are performed with an endoscope and an endoscopic biopsy instrument. An endoscopic biopsy instrument is a flexible medical device for insertion into a body passageway or cavity that enables a surgeon at a remote external location to remove and retrieve a tissue sample from a site internal to the patient's body. The biopsy instrument typically includes an elongated flexible member having a tissue sampler at the distal end and a handle assembly with a manual actuator at the proximal end.

During a biopsy tissue sampling operation, a surgeon guides the endoscope to the biopsy site within the body of the patient. The biopsy instrument is then inserted through the endoscope until the tissue sampler is proximate to the tissue to be sampled. The surgeon manipulates the actuator so that a sample of tissue is torn or cut away from the biopsy site and is retained by the tissue sampler.

The handle assembly at the proximal end of the endoscopic biopsy instrument is coupled to the tissue sampler at the distal end by an elongated flexible member. Generally, the flexible member includes a control conduit or flexible coil. A control member, typically a wire, extends through and is reciprocally movable in the proximal and distal directions within the flexible coil. The control member is attached to the manual actuator at the proximal end and to the tissue sampler at the distal end of the biopsy instrument. Operation of the actuator relative to the handle causes the control member to move relative to the flexible coil and actuate the tissue sampler.

Various apparatuses have been used to attach the flexible coil to the handle assembly. Considerations include cost, ease of component manufacture, ease of assembly, expected life cycle of the biopsy instrument, operational loads, and acceptance by the operator. Surgeons would find unacceptable any attachment apparatus that permits the flexible coil to move relative to the handle during manipulation of the end effectors.

One method of attaching the coil to the handle is bonding. This may be acceptable for disposable biopsy instruments, but not for instruments that are to be autoclaved. Repeated autoclaving may degrade the bondline. Furthermore, bonding raises OSHA/SHEA concerns regarding the exposure of assembly workers to solvent fumes.

In another example, crimping a barbed crimp band onto the end of the flexible coil and then press fitting the coil with a barbed crimp band into an inner bore of the handle is relatively expensive. Additionally, press fitting the barbed crimp band into the handle may also result in unacceptably large tensile hoop stresses in the handle that may ultimately lead to cracks. Furthermore, this design creates an undesirably large gap between the outer diameter of the flexible coil and the inner bore of the handle, leaving the flexible coil unsupported within the handle and prone to bending displacements. In instruments that incorporate an anti-kink tube for supporting the control wire at its proximal end, the bending of the flexible coil may interfere with the sliding of the anti-kink tube within the flexible coil during actuation of the actuator. This interference may subject the operator to a disagreeable grating feel and noise.

SUMMARY OF THE INVENTION

Objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

To achieve the objects and in accordance with the purpose of the invention, as embodied and broadly described herein, the invention includes an assembly connecting a flexible coil to a handle member of a endoscopic instrument. The assembly includes a handle member, a hollow nose member and a biasing element. The handle member has an inner bore. The hollow nose member has a shank configured for insertion into the inner bore and for receiving the flexible coil. The biasing element is located within the inner bore and is for biasing the flexible coil relative to the handle member.

This assembly may include a retaining element affixed to a proximal end of the flexible coil and configured for retention between the handle member and the nose member. The handle member may include one of a keyway or a projection configured for insertion into a keyway and the nose member may include the other of the keyway or the projection. The biasing element may be formed as an integral portion of the nose member, formed as an element separate from the nose member, or formed as an integral portion of the flexible coil.

In another aspect, the invention comprises an assembly for connecting a flexible coil to a handle of an endoscopic instrument, wherein the assembly includes a handle member and a hollow nose member. The handle member has an inner bore and one of a keyway or a projection configured for insertion into a keyway; the hollow nose member has a shank configured for insertion into the inner bore and for receiving the flexible coil. The nose member includes the other of the keyway or the projection.

The shank of this assembly may include a slot extending distally from the proximal end of the shank and thereby forming two resilient arms on the shank. This assembly may further include a retaining element affixed to a proximal end of the flexible coil and configured for retention between the arms of the shank. The retaining element may be integrally formed from the flexible coil.

In a further aspect, the invention comprises an endoscopic instrument having an end effector assembly, a flexible member and a handle assembly. The end effector assembly is located at the distal end of the endoscopic instrument. The flexible member is connected to and extends from the end effector assembly. The handle assembly includes a handle member having an inner bore, a hollow nose member having a shank configured for insertion into the inner bore, and a biasing element within the inner bore for biasing the flexible member relative to the handle member, wherein the flexible member is inserted into the hollow nose member and connected to the handle assembly.

The handle member of this instrument may include one of a keyway or a projection configured for insertion into a keyway, and the nose member may include the other of the keyway or the projection. The flexible member may have a retaining element affixed to an end portion opposite the end effector assembly, the retaining element configured for retention between the handle member and the nose member. The biasing element may be an integrally formed portion of the nose member; formed as an element separate from the nose member; or an integrally formed portion of the flexible member. The flexible member of this instrument may be coupled to the handle assembly by inserting the flexible member through the biasing element and through the hollow nose member thereby locating the biasing element between the nose member and the retaining element, inserting the hollow nose member, biasing element and retaining element into the inner bore of the handle member, and inserting the projections into the keyways.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention. In the drawings.

DESCRIPTION OF THE PREFERRED EMBODIMENTS

Figure 1:
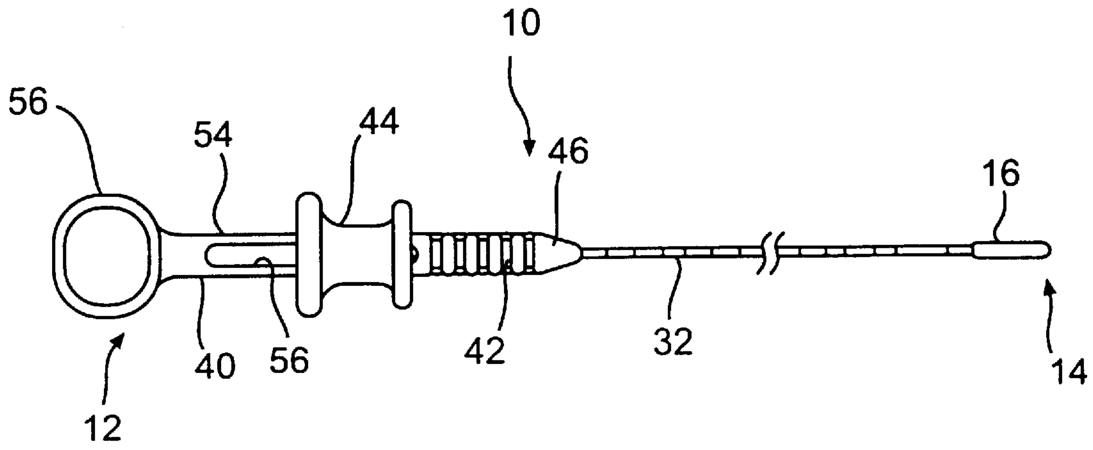
FIG. 1 is a side view of a biopsy instrument in accordance with a first embodiment of the present invention.

Reference will now be made in detail to the present preferred embodiments of the invention, examples of which are illustrated in the accompanying drawings. Wherever possible, the same reference numbers will be used throughout the drawings to refer to the same or like parts.

The present invention generally relates to an apparatus for attaching a flexible control conduit to a proximal handle assembly of an endoscopic instrument, and particularly, an endoscopic biopsy instrument. While the invention is described herein in connection with a biopsy forceps device, it is understood that the invention may be used in connection with various other endoscopic and nonendoscopic surgical instruments. According to a broad aspect of the invention, the flexible conduit is attached to the handle assembly by a nose piece. The flexible control conduit is threaded through a central bore of the nose piece and a retaining band is attached to the proximal end of the flexible control conduit that is to be retained. A compressive spring member, either an integrally formed part of the nose piece or a separate and distinct element, is located between the nose piece and the retaining band. Alternatively, the compressive spring member may be located between the retaining band and the handle assembly. The nose piece is then inserted into the handle assembly, thereby trapping both the retaining band and the compressive spring member between the nose piece and the handle assembly and compressing the spring member. The spring member biases the retaining band and the flexible control conduit against either the nose piece or the handle assembly, and at the same time, biases the nose piece away from the handle assembly. Relative axial movement between the handle assembly, nose piece, and control conduit is thus minimized or eliminated.

The present invention has other advantages over the prior art. For instance, as discussed below, the assembly of the flexible control conduit to the handle assembly does not require any bonding, and therefore overcomes the disadvantage associated with bonding, including assembly workers' exposure to solvent fumes. Moreover, no special tools are needed for assembly, the assembly process is simpler, and component misalignment during assembly can be corrected. Furthermore, a crimp band is less expensive than a barbed band and overcomes many of the disadvantages of a barbed band, such as cracking due to tensile hoop stress in the handle. Finally, also as discussed below, the flexible control conduit is fully supported within the handle assembly and bending displacement of the flexible coil is eliminated or minimized. Thus, when an anti-kink tube is used to support the proximal end of the control wire, there is no interference between the anti-kink tube and the flexible conduit as the tube slides inside the coil.

An endoscopic biopsy instrument according to the present invention generally includes an end effector assembly at a distal end, a handle assembly at a proximal end, and an elongate flexible member connecting the end effector assembly to the handle assembly. In an actuatable endoscopic biopsy instrument the handle assembly includes a manual actuator and the end effector assembly is manipulable. The flexible member of an actuatable biopsy instrument generally includes a flexible control conduit that couples the proximal handle assembly to the end effector assembly. The manual actuator and the manipulable end effector assembly also are coupled together with a control member that extends through the flexible control conduit. These general portions of the biopsy instrument will now be more specifically described. The operation of the biopsy instrument will be described thereafter.

In accordance with the invention, there is provided a biopsy instrument having a proximal end and a distal end. As embodied herein and as illustrated in FIG. 1, biopsy instrument 10 includes proximal end 12 and distal end 14. During a surgical procedure, proximal end 12 remains external to a patient's body and under the direct physical control of the surgeon. Distal end 14 is inserted into a passageway or cavity of the patient's body and is positioned proximate to the remote internal operation site. In the preferred embodiment, distal end 14 of biopsy instrument 10 is inserted into and threaded through an endoscope (not shown) which has previously been inserted into the patient's body and positioned proximate to the operation site.

Figure 2A:
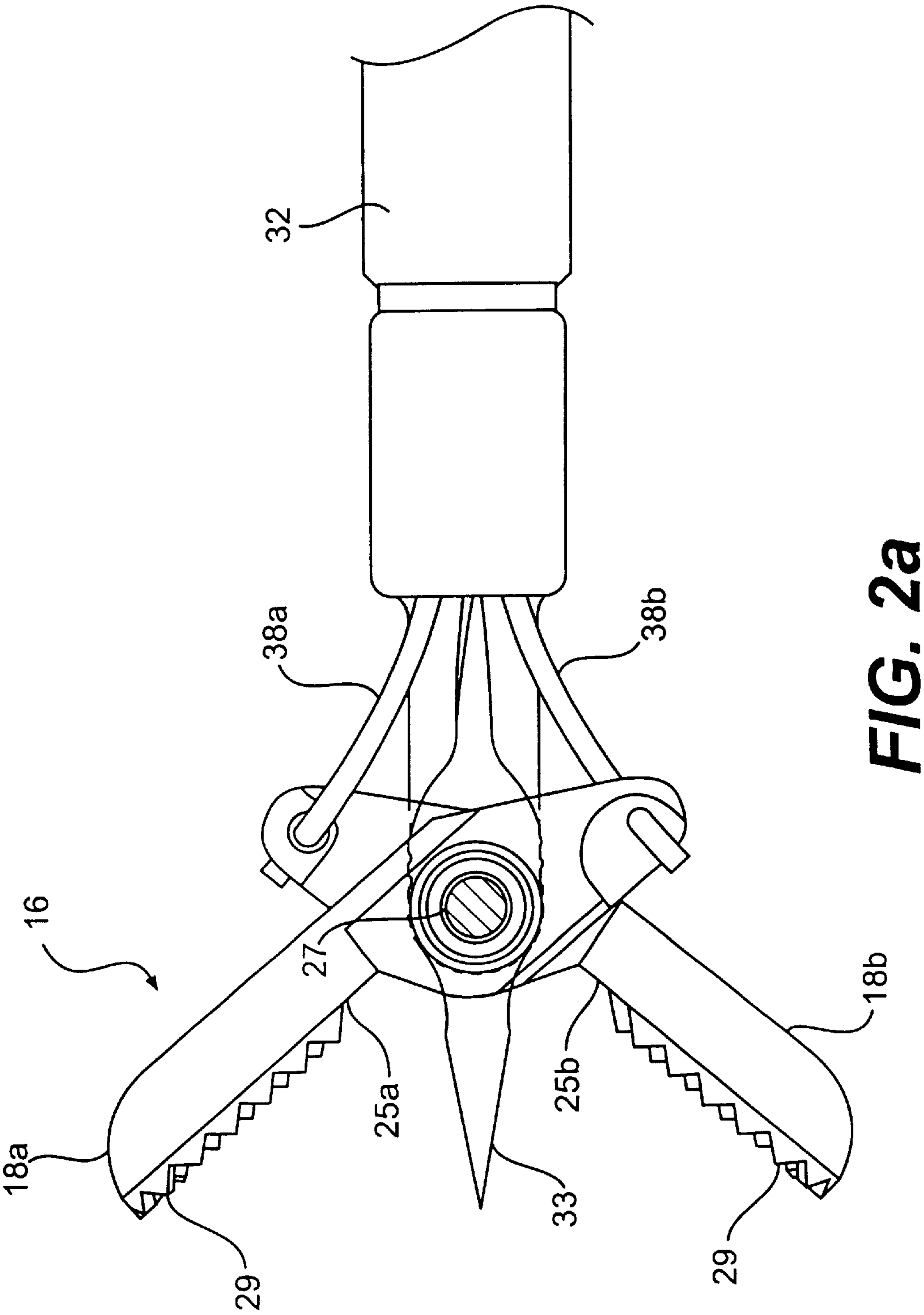
FIG. 2*a* is a side view of the end effector assembly of FIG. 1.

The biopsy instrument according to the present invention includes an end effector assembly for use in a biopsy operation. As shown in FIG. 1, an end effector assembly 16 is located at distal end 14 of biopsy instrument 10 on the distal end of a flexible member 32 opposite a handle assembly 40. As embodied herein and as best shown in FIG. 2*a*, end effector assembly 16 includes manipulable jaws 18*a*, 18*b*. Jaws 18*a*, 18*b*, coupled to the distal ends of control wires 38*a*, 38*b*, are manipulable around a central pivot pin 27. Furthermore, jaws 18*a*, 18*b* may have teeth 29 located on their inner faces 25*a*, 25*b*. Additional end effector devices may be incorporated into end effector assembly 16. For example, as shown in FIG. 2*a*, a needle 33 for stabilizing the biopsy sample prior to a detachment from the surrounding tissue may be centrally located between manipulable jaws 18*a*, 18*b*.

Figure 2B:
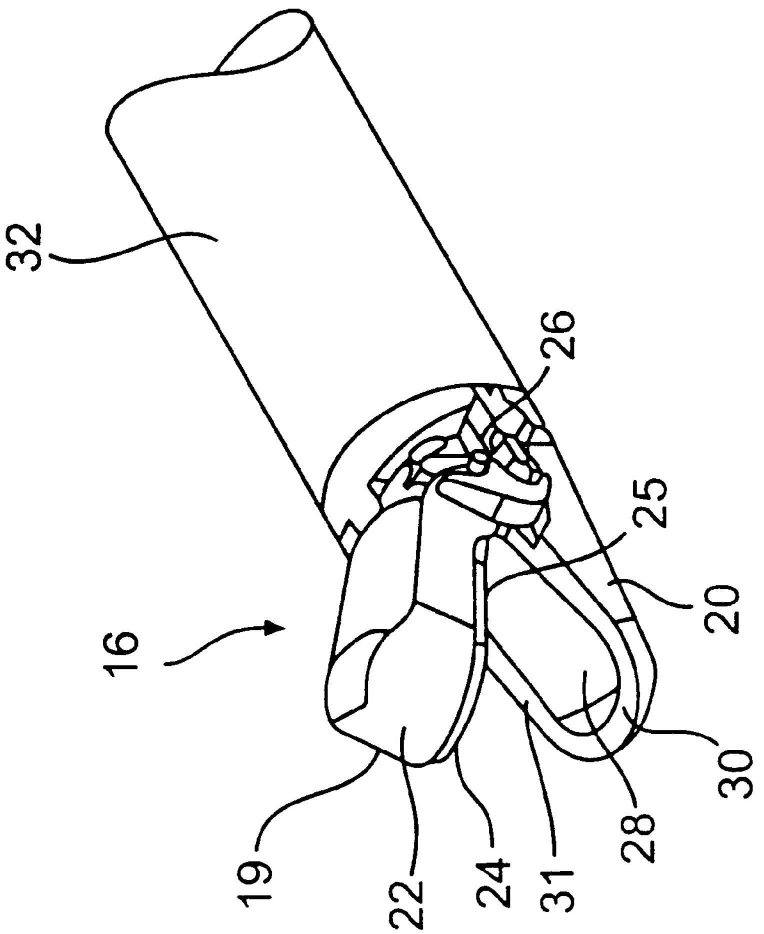
FIG. 2*b* is a perspective view of an alternate end effector assembly for use with the present invention.

It should be understood that while the above described manipulable end effector assembly may be used with a preferred embodiment of the invention, other end effectors, such as those for grasping, dissecting, or other surgical procedures, may also be used without departing from the scope or spirit of the invention. For example, as shown in FIG. 2*b*, end effector assembly 16 may include a manipulable jaw 19 and an opposing stationary jaw 20. Manipulable jaw 19 includes a cup-like body 22 and a sharp cutting edge 24 on inner face 25. Manipulable jaw 19 pivots about pivot pin 26 to urge cutting edge 24 against the stationary jaw 20. Stationary jaw 20 may include a concave cavity 28 and a blunt edge 30 on inner face 31.

Further details of manipulable jaw 19 and opposing stationary jaw 20 are disclosed in commonly assigned U.S. patent application Ser. No. 08/756,260, the complete disclosure of which is incorporated herein by reference.

Figure 3:
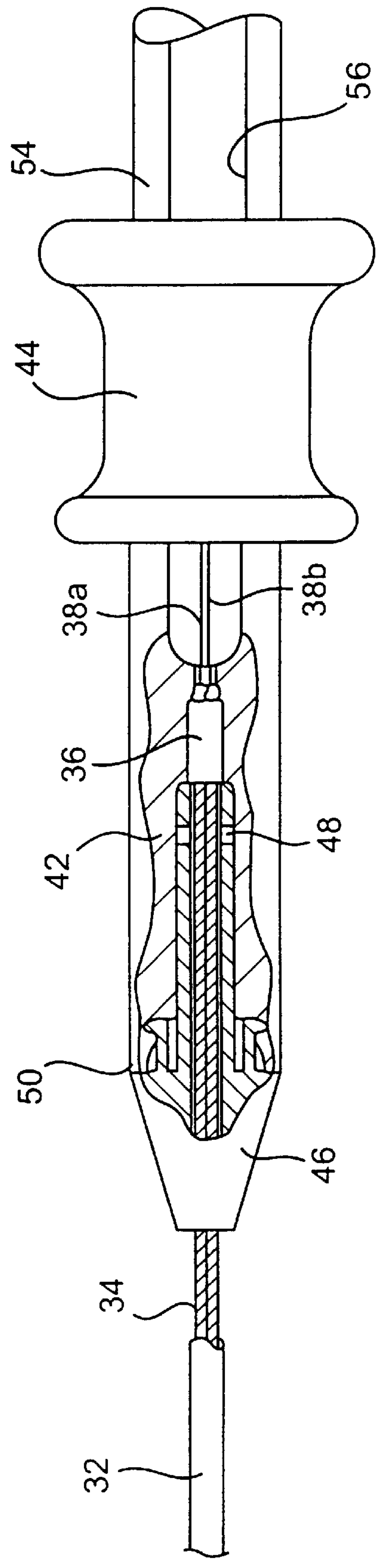
FIG. 3 is a partially cut-away side view of the handle assembly of FIG. 1.

The biopsy instrument according to the present invention also includes an elongate flexible member connected to and extending from the end effector assembly. As embodied herein and as illustrated in FIG. 1, elongate flexible member 32 extends from end effector assembly 16 at distal end 14 to handle assembly 40 at proximal end 12. As best shown in FIG. 3, elongate flexible member 32 includes flexible control conduit 34. Control conduit 34 provides a channel through which control wires 38*a*, 38*b* extend. Control conduit 34 may be a flexible coil.

In a preferred embodiment, the flexible coil of control conduit 34 is mandrel wound with a left-hand pitch and a slight preload from 0.021 inch diameter 300 series Stainless Steel diamond drawn wire. The inside diameter of the flexible coil is large enough to house a plastic liner and a pair of control wires.

Flexible control conduit 34 has a retaining element 36 affixed to its proximal end. As embodied herein and as illustrated in FIG. 3, retaining element 36 is a ferrule or crimp band. In a preferred embodiment, retaining element 36 is machined from malleable brass and is a hollow cylinder. It is crimped to the outside of flexible control conduit 34 near the proximal end of conduit 34. The attachment of flexible control conduit 34 to handle assembly 40 will be described later in greater detail.

The biopsy instrument according to the present invention also includes a control member connected to and extending from the end effector assembly. The control member includes a pair of control wires 38*a*, 38*b*. As embodied herein and as shown in FIG. 2*a*, control wires 38*a*, 38*b* connect to manipulable jaws 18*a*, 18*b* of end effector assembly 16. As shown in FIG. 3, control wires 38*a*, 38*b* extend in a proximal direction through control conduit 34 to an actuator spool 44 at proximal end 12. Although the preferred embodiment is described in connection with a pair of control wires, the concept presented herein applies equally to a single wire design.

The proximal ends of control wires 38*a* and 38*b* are connected to actuator spool 44. Axial displacement of actuator spool 44 relative to handle assembly 40 rotates manipulable jaws 18*a*, 18*b* about pivot pin 27, and thereby moves the jaws from an open position to a closed position. This configuration allows a surgeon to cut a biopsy sample by manipulating actuator spool 44. Actuator spool 44 will be described later in greater detail.

An anti-kink tube (not shown) may be used to prevent the proximal ends of control wires 38*a*, 38*b* immediately adjacent actuator spool 44 from buckling when loaded in compression. Control wires 38*a*, 38*b* are contained within the anti-kink tube. The anti-kink tube may be made from stainless steel hypodermic needle tubing stock with an outside diameter smaller than the inside diameter of flexible control conduit 34 or flexible coil. The anti-kink tube is attached at its proximal end to control wires 38*a*, 38*b*. Movement of actuator spool 44 and control wires 38*a*, 38*b* causes the anti-kink tube to slide within the proximal end of flexible control conduit 34.

In accordance with the invention, the biopsy instrument includes a handle assembly connected to the elongate flexible member at the proximal end. The embodiment shown in FIG. 1 includes handle assembly 40 located at proximal end 12 of biopsy instrument 10 and connected to elongate flexible member 32. As shown in FIG. 3, handle assembly 40 includes a gripping member 42, an actuator spool 44, a hollow nose member 46 and a biasing element 48.

Figure 5:
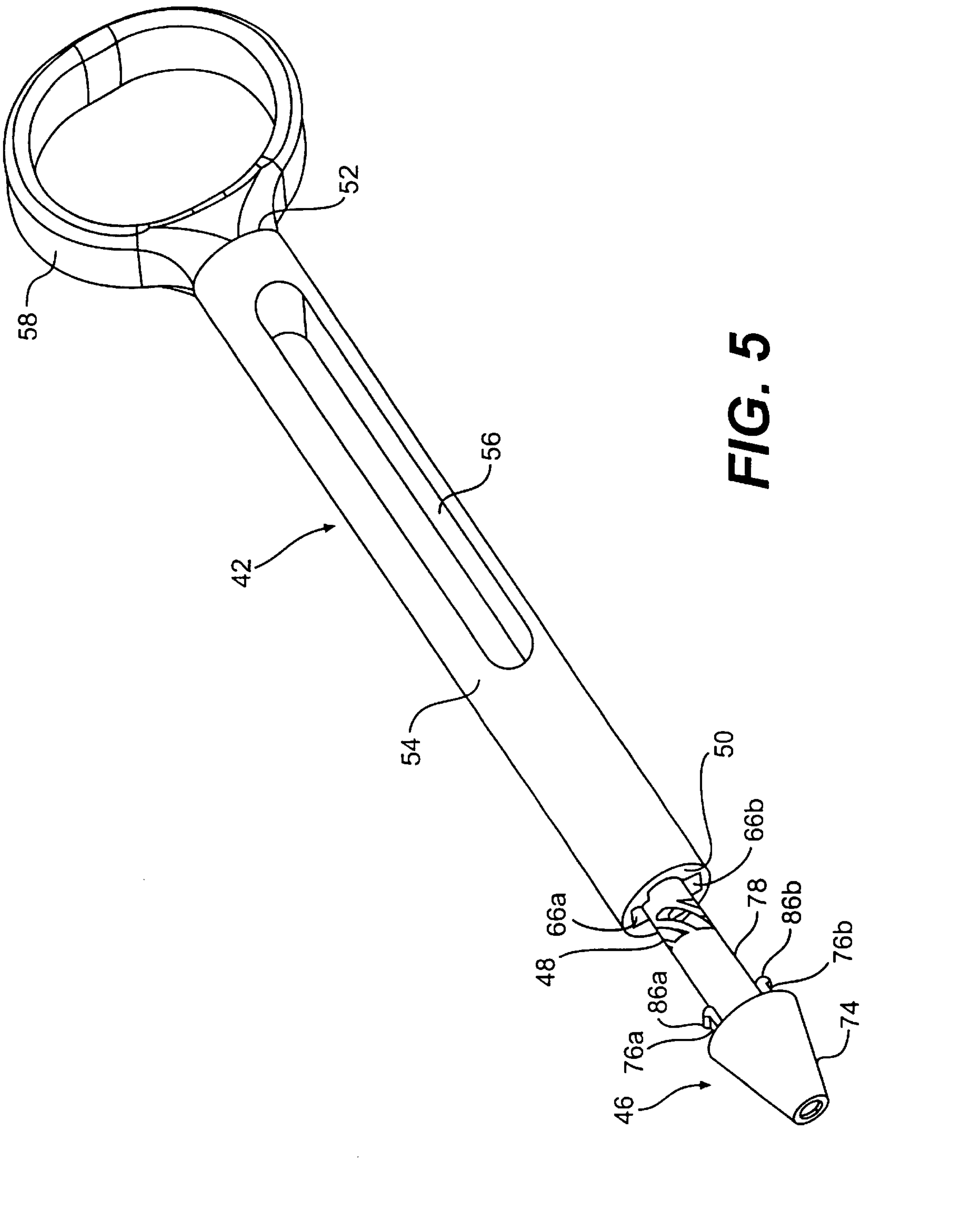
FIG. 5 is an exploded perspective view of the handle assembly and the nose member of FIG. 1.

As shown in FIG. 5, gripping member 42 has a distal end 50 and a proximal end 52. Gripping member 42 includes an elongate shaft 54 extending from distal end 50 to proximal end 52. Shaft 54 has a transverse slot 56 extending longitudinally along the central portion of shaft 54. As best shown in FIG. 3, control wires 38*a*, 38*b* extend longitudinally through the center of slot 56.

At proximal end 52 of gripping member 42, a thumb ring or manipulation ring 58 is integrally affixed to shaft 54. Manipulation ring 58 enables a surgeon to better grip and control biopsy instrument 10.

Figure 4:
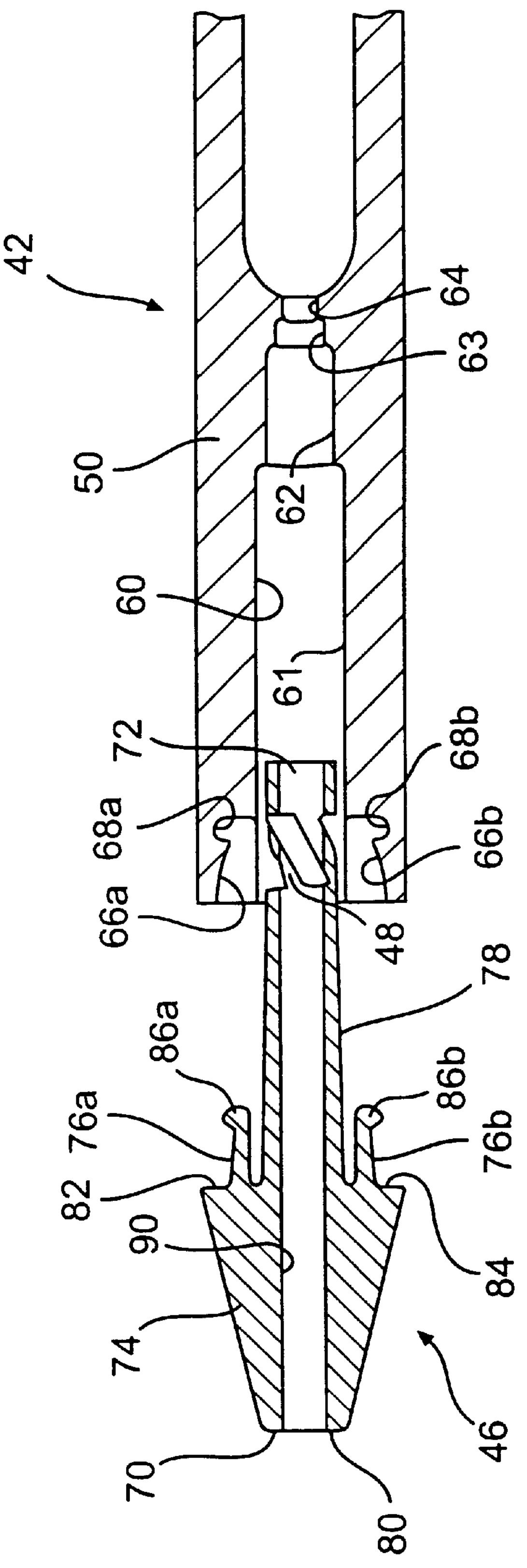
FIG. 4 is an exploded cross-sectional view of a portion of the handle assembly and the nose member of FIG. 1.

As illustrated in FIG. 4, at distal end 50 of gripping member 42, shaft 54 has a quadruple stepped throughbore 60. A first portion 61 is sized to accommodate the insertion of a hollow nose member 46, as will be described below. In a preferred configuration, first portion 61 is rectangular in cross-section, although a square or circular cross-section may be used. First portion 61 may also be somewhat tapered to provide easier removal from a mold used during the manufacturing process. The diameter of a second portion 62 is sized to accept retaining element 36. The length of second portion 62 is slightly less than the length of retaining element 36, so that members inserted into first portion 61 will come into positive contact with retaining element 36 rather than the back wall of first portion 61. A third portion 63 is sized to accept the flexible coil or control conduit 34. Third portion 63 has a diameter slightly larger than the outer diameter of control conduit 34. A fourth portion 64 of stepped throughbore 60 is sized to assist in guiding the anti-kink tube into the inner diameter of control conduit 34. Fourth portion 64 has a diameter approximately equal to the inner diameter of control conduit 34.

Stepped throughbore 60 need not be quadruple stepped. For instance, as shown in FIGS. 12*e* and 12*f*, second portion 62 has been eliminated. Additionally, although third portion 63 is illustrated in FIGS. 12*e* and 12*f*, third portion 63 may be eliminated without affecting the operation of the present invention. The number of steps in throughbore 60 and other such design considerations may altered without violating the spirit of the invention.

In a preferred embodiment as shown in FIG. 4, a pair of diametrically opposed keyways 66*a*, 66*b* are located on the distal end 50 of gripping member 42. Keyways 66*a*, 66*b* extend longitudinally into the wall which defines first portion 61 of throughbore 60. The interior ends of keyways 66*a*, 66*b* have notches 68*a*, 68*b* projecting radially outward, respectively. Notches 68*a*, 68*b* may extend through the outer wall of gripping member 42, thus becoming holes rather than notches.

Notches are preferred for cosmetic purposes and to guard against accidental disconnection. Alternatively, keyways 66*a*, 66*b* may be located closer to the outer wall of gripping member 42 and notches 68*a*, 68*b* may project radially inward.

Gripping member 42 is preferably an injection molded plastic part. One preferred material is acrylonitrile butadiene-styrene (ABS), although other materials may serve as well.

As embodied herein and as shown in FIGS. 1 and 3, handle assembly 40 also includes manipulable actuator spool 44 connected to end effector assembly 16 via control wires 38*a*, 38*b*. As illustrated in FIG. 3, actuator spool 44 includes a hole through which shaft 54 extends. This configuration permits spool 44 to reciprocally slide proximally and distally along the length of shaft 54. Actuator spool 44 also has a transverse bar (not shown) extending through slot 56 of shaft 54. Control wires 38*a*, 38*b* connect to the midpoint of the transverse bar. Thus, sliding actuator spool 44 back and forth along the length of shaft 52 causes axial displacement of control wires 38*a*, 38*b* relative to control conduit 34. Such relative displacement actuates manipulable jaws 18*a*, 18*b* of end effector assembly 16. It is to be understood that various other suitable actuation devices known to one skilled in the art may be used in connection with the present invention. For example, as alternatives, the actuation device may be embodied as a three-ring device, a scissor handle, a pistol grip, or any other structure which permits a surgeon to move the control member relative to the handle. Additionally, various other methods may be used to attach control wires 38*a*, 38*b* to actuator spool 44.

In accordance with the present invention, the handle assembly also includes a hollow nose member. As embodied herein and as illustrated in FIG. 4, handle assembly 40 includes hollow nose member 46 having a distal end 70 and a proximal end 72. A longitudinal axis extends from distal end 70 to proximal end 72. Nose member 46 is preferably an injection molded plastic part. One preferred material is ABS, although other materials may serve as well.

As shown in FIGS. 4 and 5, nose member 46 has a hollow frustoconical tip 74 at distal end 70 connected to resilient cantilevered projections 76*a* and 76*b* and to a shank portion 78. Frustoconical tip 74 has a smaller diameter front surface 80 and a larger diameter back surface 82. Back surface 82 is greater in diameter than the diameter of stepped throughbore 60 of gripping member 42. Back surface 82 defines a stop flange 84. Alternatively, tip 74 may be hemispherical, blunt or any other suitable shape.

Resilient cantilevered projections 76*a*, 76*b* extend in a roughly longitudinal direction from back surface 82 of frustoconical tip 74. Teeth 86*a*, 86*b*, projecting radially outward, are provided at the free end of each of cantilevered projections 76*a*, 76*b*, respectively. Cantilevered projections 76*a*, 76*b* are configured to complement keyways 66*a*, 66*b*, respectively; teeth 86*a*, 86*b* are configured to engage notches 68*a*, 68*b* respectively.

In an alternative configuration (not shown), the projections, as opposed to the keyways, may be provided on the distal end of the gripping member. In this configuration, the keyways, as opposed to the projections, would be provided on the back surface of the frustoconical tip of the hollow nose member.

Hollow shank portion 78 extends in a longitudinal direction from back surface 82 of frustoconical tip 74. The cross-section of shank portion 78 complements the cross-section of first portion 61 of stepped throughbore 60. The length of shank portion 78 is less than the length of first portion 61 by an amount that accounts for the length of the retaining element 36 and the compressed length of the biasing element 48.

A cylindrical inner bore 90 extends through hollow nose member 46. Inner bore 90 is sized to provide minimal diametrical clearance between the outer diameter of flexible control conduit 34 and the diameter of inner bore 90. Inner bore 90 may be sized to accommodate different size control conduits, jacketed and non-jacketed conduits, different jacket thicknesses, etc. In addition, the diameter of inner bore 90 is less than the outer diameter of retaining element 36, thereby denying retaining element 36 passage through shank portion 78.

Minimizing the clearance between control conduit 34 and inner bore 90 helps to fully support the portion of conduit 34 within gripping member 42. The more fully supported conduit 34 is, the less it will bend during operation. A straight control conduit 34 allows the anti-kink tube to slide freely within control conduit 34 without striking the inner wall of conduit 34 or causing a disagreeable grating to be heard and felt by the surgeon during use of the instrument.

Figure 11A:
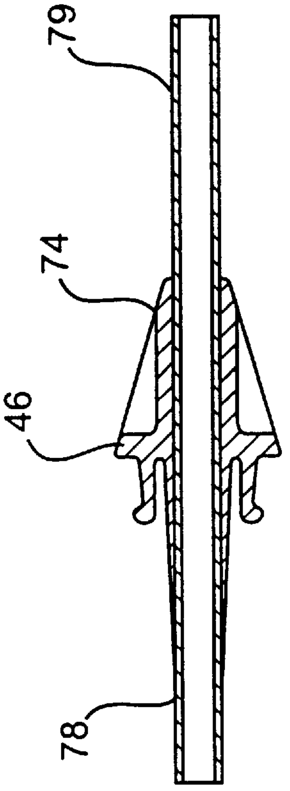
FIG. 11*a* is a cross-sectional view of the nose member in accordance with still another embodiment of the present invention.

Moreover, the flexible coil may be provided with a strain relief to prevent kinking of the flexible coil immediately adjacent handle assembly 40. In a first aspect, a separate strain relief piece of plastic tubing (not shown), preferably made of polyurethane or heat shrink material, may be fitted over the flexible coil near the proximal end of the coil. This strain relief tubing may extend approximately two inches over the flexible coil both within proximal handle assembly 40 and immediately adjacent handle assembly 40. In an alternative aspect, the strain relief may be integrally molded with nose member 46. As shown in FIG. 11*a*, nose member 46 may be provided with a strain relief portion 79 extending in a distal direction from the distal end of tip 74. Nose member 46 may be manufactured by a process called "insert molding," i.e., by placing a length of conventionally extruded plastic tubing within the cavity of the nose member mold, closing the mold, and injecting plastic resin around the tubing. In this manner shank portion 78 and strain relief portion 79 may be formed from the extruded plastic tubing.

Figure 11B:
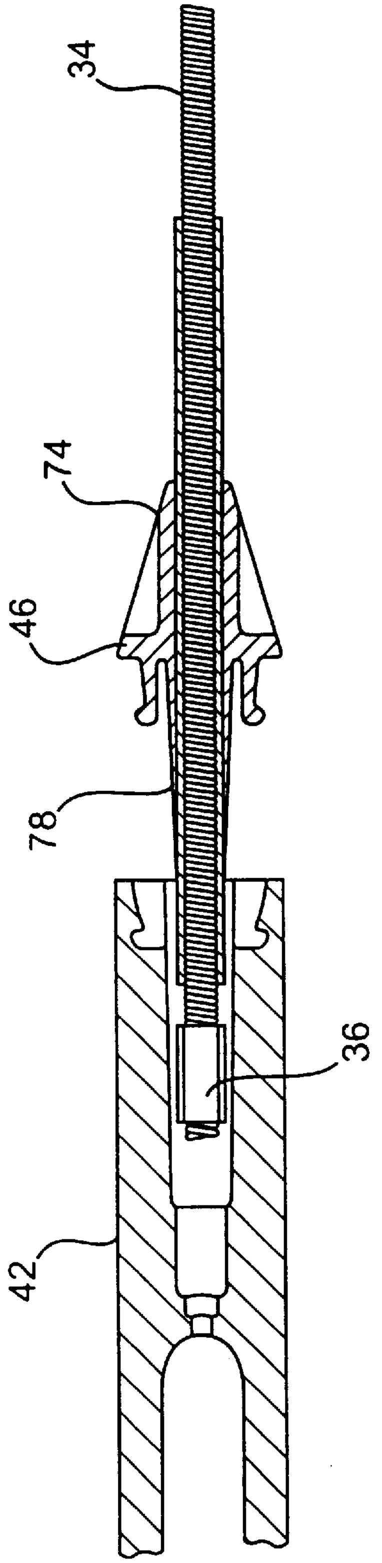
FIG. 11*b* is an exploded partial cross-sectional view of a portion of the handle assembly in accordance with the embodiment of FIG. 11*a;*

Alternatively, shank portion 78 may be formed from both the extruded plastic tubing and an additional layer of plastic resin injection molded over the tubing. As shown in FIG. 11*b*, control conduit 34 may be inserted through shank portion 78, tip 74, and strain relief portion 79, and this subassembly may be inserted and snapped into the distal end of gripping member 42.

The flexible coil also may be fully or partially sheathed or jacketed with a plastic or polymer such as polyolefin. This jacket serves as a lubricious coating that improves the ease of inserting biopsy instrument 10 into the endoscope. In electrocautery capable embodiments, this jacket may also function as an electrical insulator between biopsy instrument 10 and its environment. Furthermore, this jacket may serve the same function as the strain relief described above, thus allowing the strain relief to be omitted.

In accordance with the present invention, the handle assembly may include a biasing element. Biasing element 48 is a compressively resilient element that compensates for tolerance stack-up between gripping member 42, nose member 46 and retaining element 36. Biasing element 48 removes the play in the attachment of flexible control conduit 34 to handle assembly 40 by biasing nose member 46 away from both control conduit 34 and gripping member 42. Typical deflections of biasing element 48 may range from 0.0 to 0.040 inches. Typical loads developed when biasing element 48 is compressed through the above deflections may range from 1.0 to 4.0 pounds. It is to be understood that deviations from these deflections and loads fall within the scope of the present invention.

Figure 6:
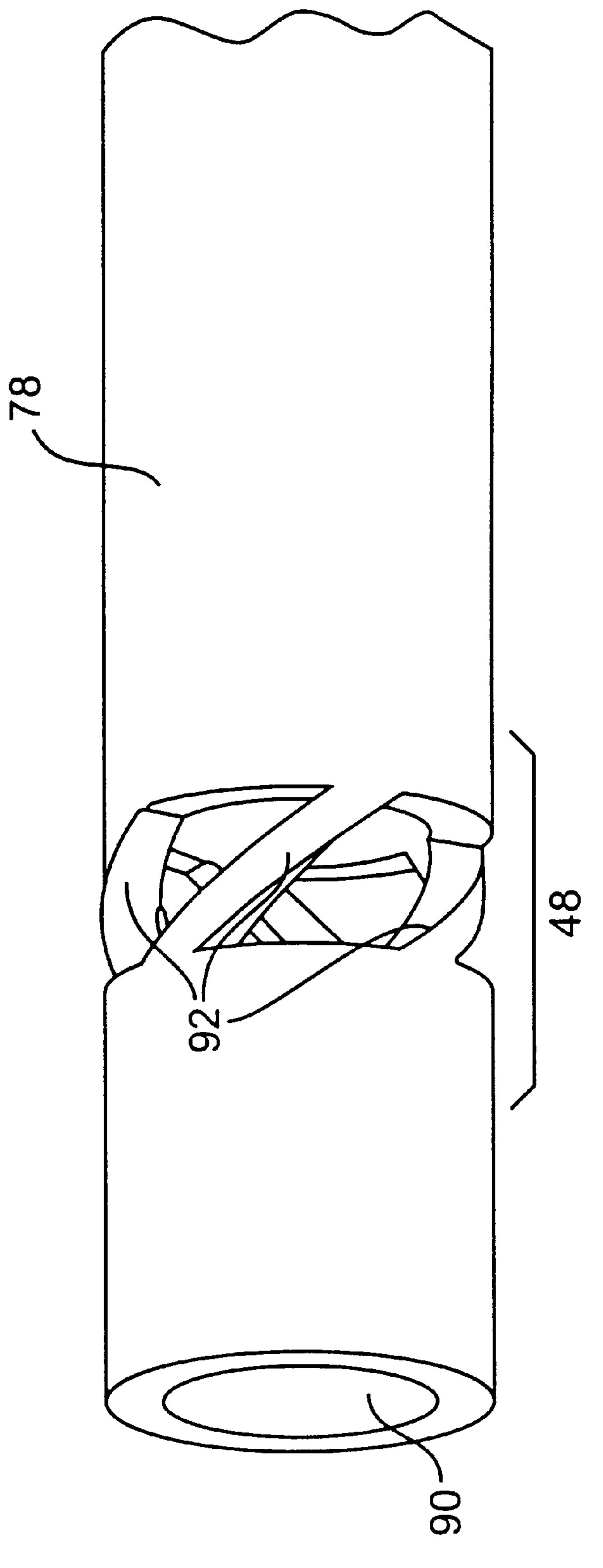
FIG. 6 is a perspective view of a detail of the nose member of FIG. 5.

In the embodiments as shown in FIGS. 3–7, biasing element 48 is an integrally formed portion of shank portion 78. In the embodiment of FIGS. 3–6, and as best shown in FIG. 6, biasing element 48 may include parallel leaf springs 92 integrally molded into shank portion 78 of the same material as shank portion 78. In a preferred configuration of this embodiment, biasing element 48 includes four parallel leaf springs 92. If shank portion 78 has a cylindrical cross-section, then leaf springs 92 may assume a helical undeformed configuration. If shank portion 78 has a hollow rectangular cross-section, then leaf springs 92 may be straight in their undeformed configuration. Each individual leaf spring 92 may have any cross-section consistent with the desired spring constant of biasing element 48.

Figure 7:
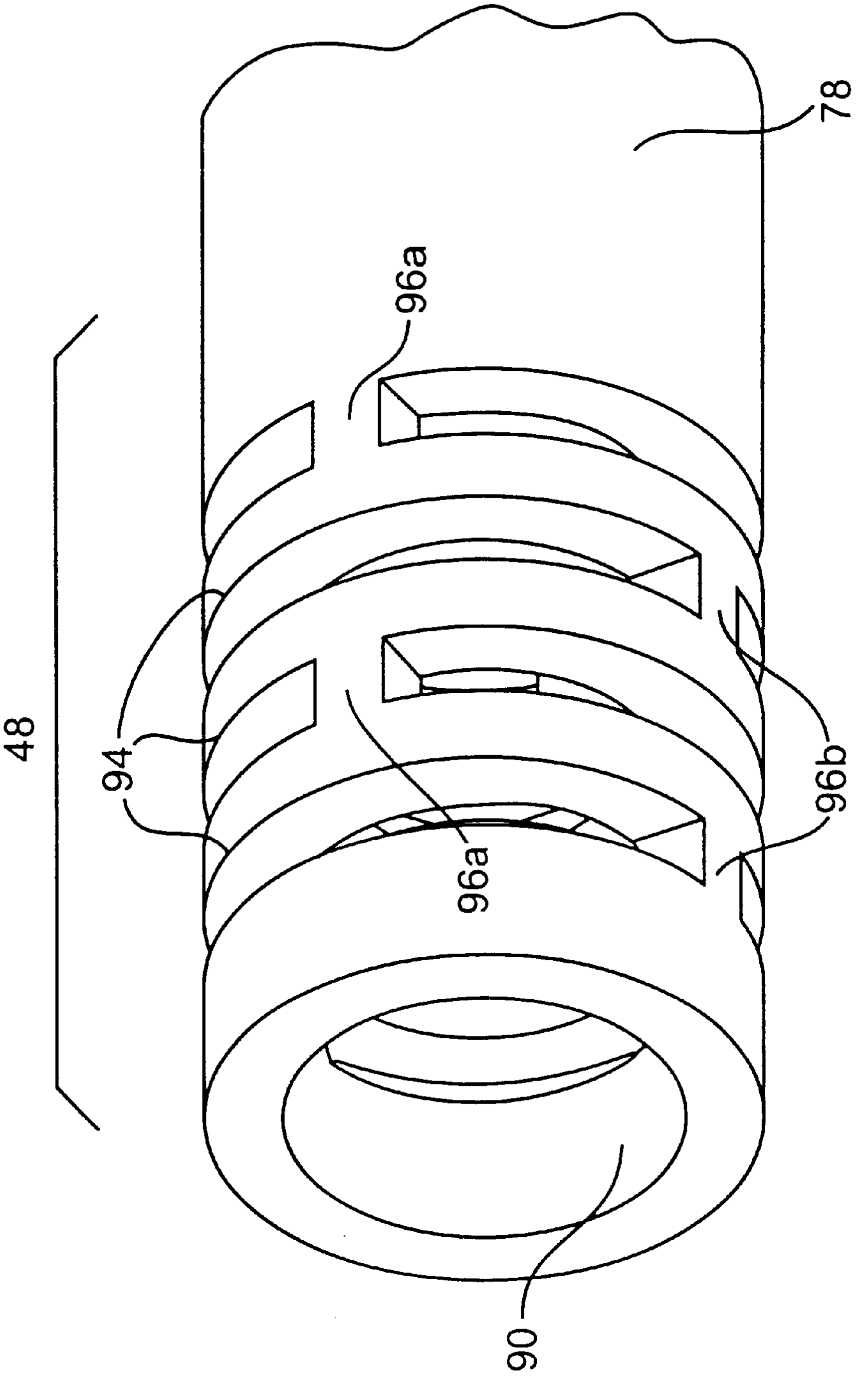
FIG. 7 is a perspective view of a detail of the nose member of an alternative embodiment of the present invention.

Alternatively, in the embodiment shown in FIG. 7, biasing element 48 may include a plurality of circumferential rings 94 separated by supports 96*a* and 96*b*, again, integrally molded into shank portion 78 of the same material as shank portion 78. Supports 96*a* and 96*b* are rotationally offset from adjacent pairs of supports, typically with an offset of ninety degrees. A compressive axial load on shank portion 78 causes the unsupported portions of rings 94 to bend, thereby allowing shank portion 78 to compress and develop a corresponding spring load.

Another alternative for biasing element 48 consists of a helical compression spring (not shown), again, integrally molded into shank portion 78 of the same material as shank portion 78.

A still further possible alternative for biasing element 48 includes providing the entire shank portion 78 with an inherent elasticity so that a properly dimensioned shank portion 78 provides the biasing force. As shown in FIGS. 11*a* and 11*b*, and as described previously, shank portion 78 may be formed from extruded plastic tubing, or from both extruded plastic tubing and an additional layer of plastic resin injection molded over the tubing. In the configuration of FIGS. 11*a* and 11*b*, the inherent elasticity of shank portion 78 provides the biasing force. Similarly, as shown in FIGS. 12*a*–12*f*, the inherent elasticity of the segment of shank portion 78 located between retaining element 36 and tip 74 provides the biasing force.

Yet another alternative for biasing element 48 includes providing a section of shank portion 78 with a reduced cross-sectional area (not shown), this section having an inherent elasticity that provides the biasing force.

Figure 8:
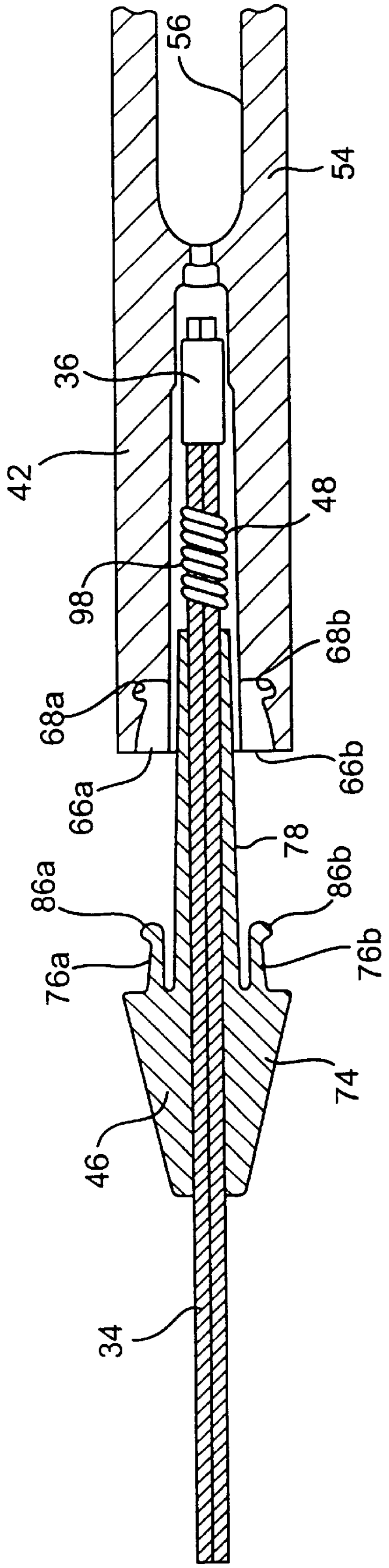
FIG. 8 is an exploded partial cross-sectional view of a portion of the handle assembly in accordance with a further embodiment of the present invention.
Figure 9:
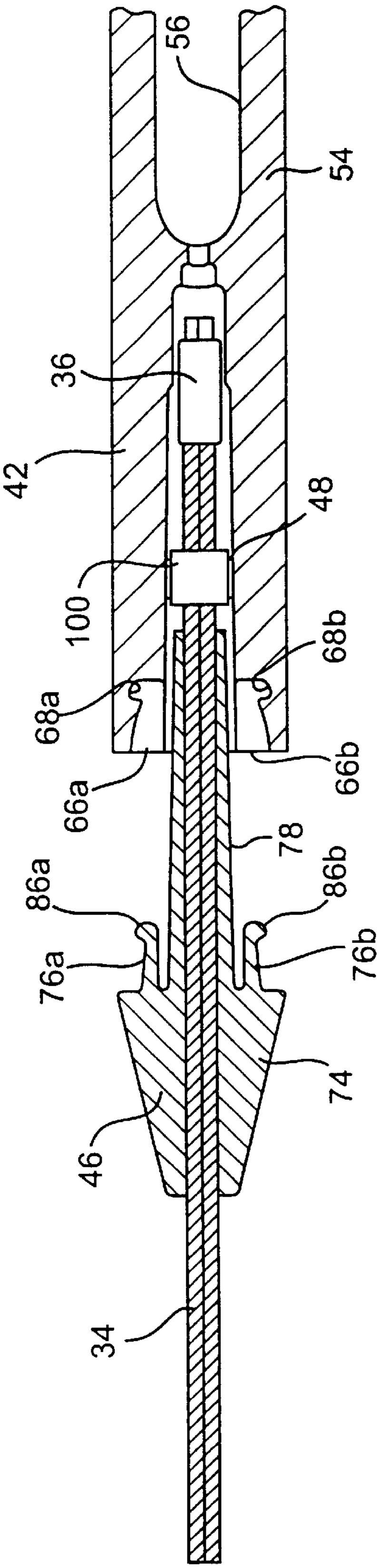
FIG. 9 is an exploded partial cross-sectional view of a portion of the handle assembly in accordance with another embodiment of the present invention.

In further embodiments as shown in FIGS. 8 and 9, biasing element 48 is formed as an element separate from shank portion 78. In the embodiment shown in FIG. 8, biasing element 48 may include a metal or plastic helical compression spring 98. Alternatively, in the embodiment shown in FIG. 9, biasing element 48 may include a resilient elastomeric spacer 100. Elastomeric spacer 100 may be made of polyurethane, silicone rubber, or other polymers with sufficiently low durometer values.

In each of the embodiments, biasing element 48 has a central through hole. In the embodiments wherein biasing element 48 is integrally molded into shank portion 78, the diameter of the central through hole of biasing element 48 is the same as the diameter of inner bore 90. The through hole is sized to accommodate flexible control conduit 34.

In the embodiments wherein biasing element 48 is a separate and distinct element, the diameter of the central through hole may depend upon the placement of biasing element 48 relative to retaining element 36. As shown in FIG. 8, if biasing element 48 is located between retaining element 36 and nose member 46, then the central through hole must be sized to accommodate flexible control conduit 34. Alternatively, if biasing element 48 is located between retaining element 36 and gripping member 42, then the central through hole need be sized to accommodate the passage of the anti-kink tube.

Figure 10:
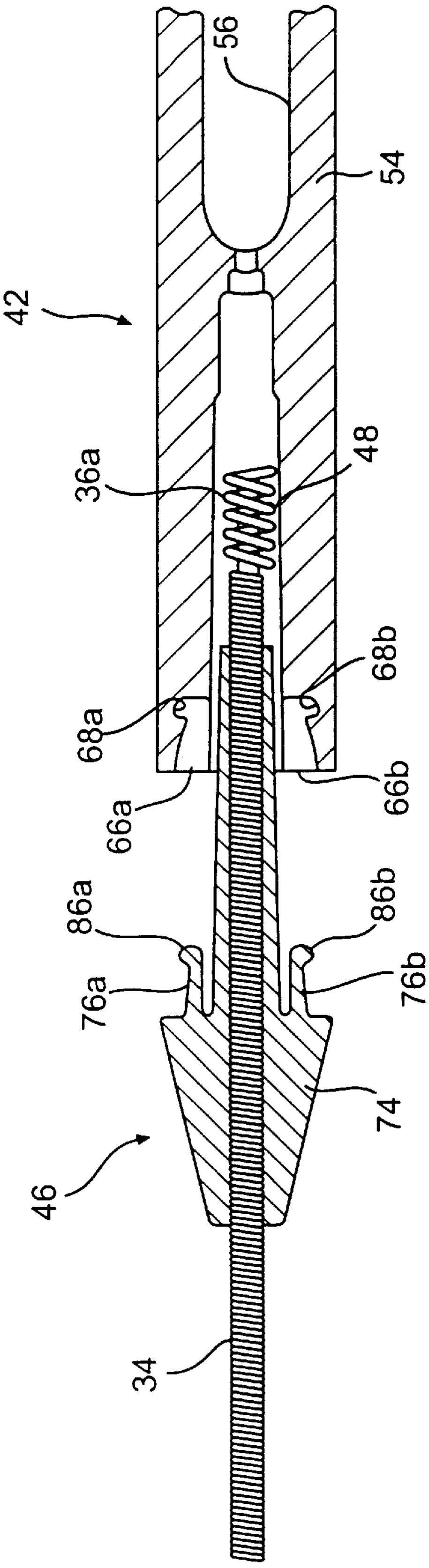
FIG. 10 is an exploded partial cross-sectional view of a portion of the handle assembly in accordance with yet another embodiment of the present invention.

In a further embodiment of the present invention, biasing element 48 is a portion of flexible control conduit 34, wherein control conduit 34 is a flexible coil. As shown in FIG. 10, a coil segment at the extreme proximal end of the flexible coil is wound with a larger diameter and an open pitch. The larger diameter of this segment precludes the flexible coil from sliding through the nose bore, and thus, this segment of the flexible coil serves as retaining element 36. The open pitch functions as a coil spring biasing element, and thus, this segment of the flexible coil also serves as resiliently compressive biasing element 48. Alternatively, this segment may be wound with a larger diameter, but without opening the pitch, without violating the spirit of the invention. In such an instance, the segment would only function as retaining element 36.

Assembly of a handle assembly according to the invention will now be described. As illustrated in FIGS. 3, 8, and 9, flexible control conduit 34 is threaded through cylindrical bore 90 of nose member 46. Retaining element 36 is attached to the end of flexible control conduit 34 that is to be retained. Biasing element 48, either an integral part of nose member 46 or a separate and distinct element, is located either between nose member 46 and retaining element 36 or between retaining element 36 and gripping member 42. Retaining element 36 and biasing element 48 are thereby trapped between nose member 46 and gripping member 42, and in the process, biasing element 48 is compressed. Depending on the location of biasing element 48, biasing element 48 pushes retaining element 36 and flexible control conduit 34 against either nose member 46 or gripping member 42, and at the same time, pushes nose member 46 away from gripping member 42.

Figure 12A:
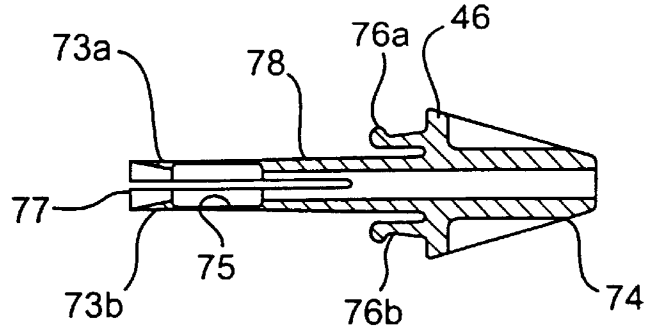
FIG. 12*a* is a cross-sectional view of the nose member in accordance with a still further embodiment of the present invention.
Figure 12B:
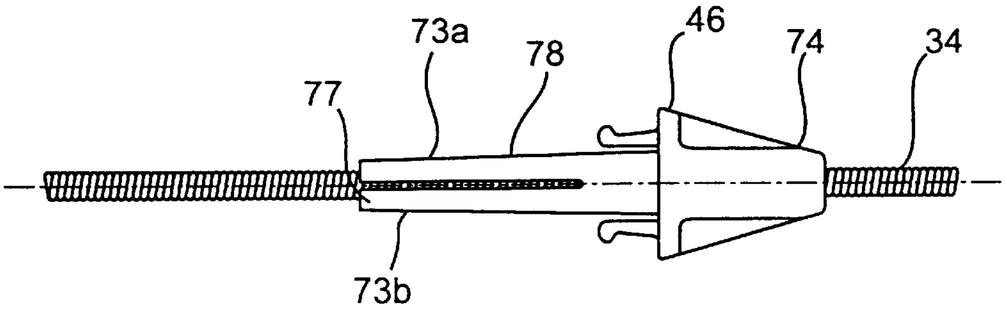
FIGS. 12*b*–12*f* are views of portions of the handle assembly in various stages of assembly in accordance with the embodiment of FIG. 12*a.*
Figure 12C:
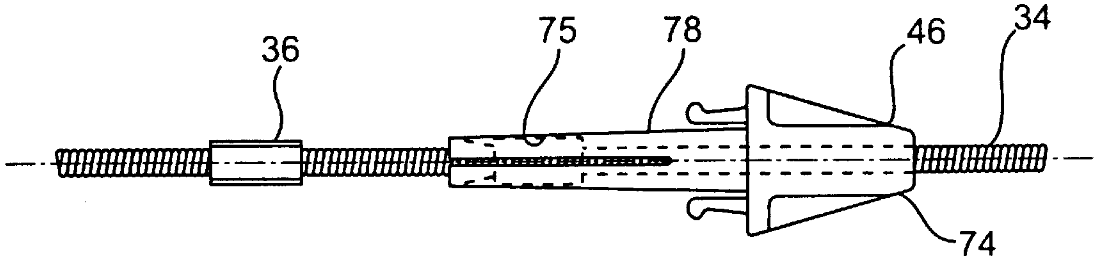
Figure 12D:
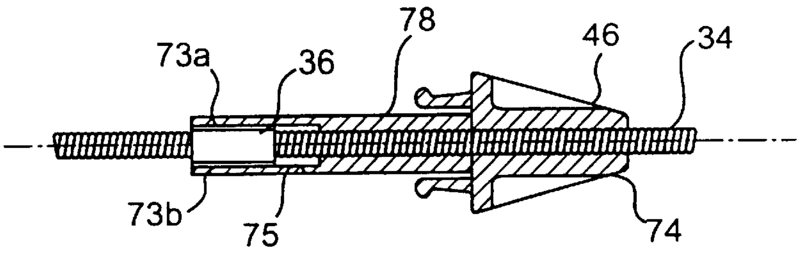
Figure 12E:
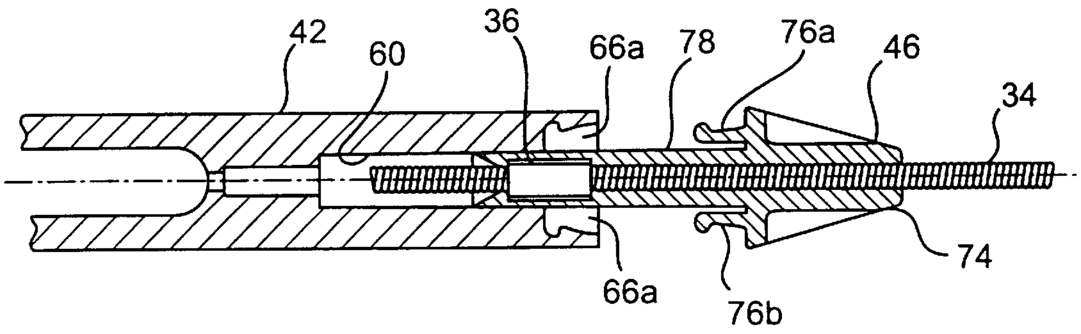
Figure 12F:
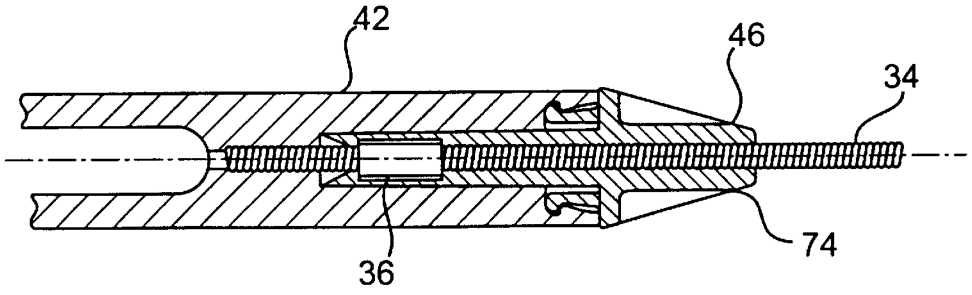

In a still further embodiment of the present invention, and as shown in FIGS. 12*a*–12*f*, shank portion 78 of nose member 46 is configured to accommodate retaining element 36. As best shown in FIG. 12*a*, shank portion 78 may be provided with slot 77 extending distally from the proximal end of shank portion 78 substantially the entire length of shank portion 78 forming two resilient arms 73*a*, 73*b*. Arms 73*a*, 73*b* have opposing semi-cylindrical walls and may be provided with chamfers on their inner surfaces at their proximal ends. Proximate the proximal end of shank portion 78, a seat 75 is provided for retaining element 36. Seat 75, located on inner bore 90 of shank portion 78, complements the outer surface of retaining element 36. Slot 77 permits shank portion 78 to expand, i.e., arms 73*a*, 73*b* to deflect radially outward, when retaining element 36 is positioned within seat 75.

As shown in FIGS. 12*b*–12*f*, flexible control conduit 34 is inserted through nose 45 member 46. Retaining element 36 is fastened to the proximal end of control conduit 34. Control conduit 34 is then moved distally, relative to nose member 46, until retaining element 36 is positioned within seat 75. During this step, arms 73*a*, 73*b* deflect radially outward over retaining element 36 and then snap back into an undeflected configuration capturing retaining element 36 in seat 75. Shank portion 78, with retaining element 36 encompassed, is then inserted into throughbore 60 of gripping member 42. When shank portion 78 is fully inserted into throughbore 60, the close fit between shank portion 78 and throughbore 60 circumferentially compresses shank portion 78, further enhancing the grip of shank portion 78 on retaining element 36. Moreover, shank portion 78 is frictionally gripped by throughbore 60. Cantilevered projections 76*a*, 76*b* of nose member 46 are then snapped into keyways 66*a*, 66*b* of gripping member 42. Relative axial movement between gripping member 42, nose member 46, and control conduit 34 is minimized.

With reference to FIGS. 1–3, when a surgeon desires to take a tissue sample from within a patient's body with minimally invasive surgery, the surgeon inserts distal end 14 of biopsy instrument 10 into an orifice of a patient under treatment. While retaining control of handle assembly 40 at proximal end 12, the surgeon guides end effector assembly 16 through the patient's body to a position adjacent a tissue to be sampled. In a preferred embodiment, the surgeon uses endoscopic technology to ensure proper positioning of the end effector assembly. The surgeon inserts distal end 14 of biopsy instrument 10 into an endoscope already inserted and properly located within a patient's body. End effector assembly 16 is threaded through the endoscope until the surgical site is reached.

At the surgical site, manipulable jaws 18*a*, 18*b* are opened and then positioned around the tissue to be sampled. The surgeon then proceeds to slide actuator spool 44 along shaft 54 of handle assembly 40 in the proximal direction. This, in turn, axially displaces control wires 38*a*, 38*b* in the proximal direction relative to control conduit 34, causing manipulable jaws 18*a*, 18*b* to pivot about pivot pin 27. End effector assembly 16 is thereby closed, and a tissue sample is separated from the surrounding tissue when teeth 29 of manipulable jaw 18*a* comes into contact with teeth 29 of manipulable jaw 18*b*. The surgeon may then withdraw distal end 14 of biopsy instrument 10 from the body of the patient in order to recover the tissue sample. A similar procedure is used in connection with the end effector assembly shown in FIG. 2*b*.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A conduit and handle assembly for use with a surgical instrument, the assembly comprising:

a flexible conduit;

a handle member having an, inner bore and one of a keyway or a projection configured for insertion into a keyway;

a hollow nose member having a shank configured for insertion into the inner bore and for receiving the flexible conduit, the nose member including the other of the keyway or the projection, wherein the shank is provided with a slot extending distally from the proximal end of the shank thereby forming two resilient arms; and a retaining element configured for retention between the arrays of the shank and integrally formed from the flexible conduit.

2. A conduit and handle assembly for use with a surgical instrument, the assembly comprising:

a flexible conduit;

a handle member having an inner bore and one of a keyway or a projection configured for insertion into a keyway; and a hollow nose member having a shank configured for insertion into the inner bore and for receiving the flexible conduit, the nose member including the other of the keyway or the projection, the nose member further including a strain relief element extending distally from the distal end of the nose member, wherein the strain relief element is integrally molded to the nose member.

3. An assembly for connecting a flexible conduit to a handle of a surgical instrument comprising:

a handle member having an inner bore;

a hollow nose member having a shank configured for insertion into the inner bore and for receiving the flexible conduit;

a biasing element within the inner bore for biasing the flexible conduit relative to the handle member; and a retaining element integrally formed from the proximal end of the flexible conduit and configured for retention between the handle member and the nose member.

4. An assembly for connecting a flexible conduit to a handle of a surgical instrument comprising:

a handle member having an inner bore;

a hollow nose member having a shank configured for insertion into the inner bore ard for receiving the flexible conduit; and a biasing element within the inner bore for biasing the flexible conduit relative to the handle member, the biasing element being compressible, an integrally formed portion of the shank of the nose member, and including a plurality of ring integrally molded into the shank, the rings stacked with offsets therebetween, aid capable of out-of-plane bending.

5. An assembly for connecting a flexible conduit to a handle of a surgical instrument comprising:

a handle member having an inner bore;

a hollow nose member having a shank configured for insertion into the inner bore and for receiving the flexible conduit; and a biasing element within the inner bore for biasing the flexible conduit relative to the handle member, wherein the biasing element is an elastomeric ring formed as an element separate from the nose member.

6. An assembly for connecting a flexible conduit to a handle of a surgical instrument comprising:

a handle member having an inner bore;

a hollow nose member having a shank configured for insertion into the inner bore and for receiving the flexible conduit; and a biasing element within the inner bore for biasing the flexible conduit relative to the handle member, the biasing element located between the nose member and a retaining element configured for being affixed to a proximal end of the flexible conduit.

7. An assembly for connecting a flexible conduit to a handle of a surgical instrument comprising:

a handle member having an inner bore;

a hollow nose member having a shank configured for insertion into the inner bore and for receiving the flexible conduit; and a biasing element within the inner bore for biasing the flexible conduit relative to the handle member, the biasing element being an integrally formed portion of the flexible conduit.

8. An endoscopic instrument having a proximal end and a distal end, the endoscopic instrument comprising:

an end effector assembly at the distal end of the endoscopic instrument;

a flexible member connected to and extending from the end effector assembly; and a handle assembly including a handle member having an inner bore, a hollow nose member having a shank configured for insenion into the inner bore, and a biasing element within the inner bore for biasing the flexible member relative to the handle member, wherein the flexible member is inserted into the hollow nose member and connected to the handle assembly and wherein the biasing element is a compressible, integrally formed portion of the shank of the nose member that includes a plurality of rings integrally molded into the shank, the rings stacked with offset supports therebetween and capable of out-of-plane bending.

9. An endoscopic instrument having a proximal end and a distal end, the endoscopic instrument comprising:

an end effector assembly at the distal end of the endoscopic instrument;

a flexible member connected to aid extending from the end effector assembly; and a handle assembly including a handle member having an inner bore, a hollow nose member having a shank configured for insertion into the inner bore, and a biasing element within the inner bore for biasing the flexible member relative to the handle member, wherein the flexible member is inserted into the hollow nose member and connected to the handle assembly, wherein the biasing element is formed as an element separate from the nose member, wherein the biasing element is an elastomeric ring.

10. An endoscopic instrument having a proximal end and a distal end, the endoscopic instrument comprising:

an end effector assembly at the distal end of the endoscopic instrument;

a flexible member connected to and extending from the end effector assembly; and a handle assembly including a handle member having an inner bore, a hollow nose member having a shank configured for insertion into the inner bore, and a biasing element within the inner bore for biasing the flexible member relative to the handle member, wherein the flexible member is inserted into the hollow nose member and connected to the handle assembly and wherein the biasing element is formed as an element separate from the nose member that is located between a retaining element affixed to a proximal end of the flexible member and the nose member.

11. An endoscopic instrument having a proximal end and a distal end, the endoscopic instrument comprising:

an end effector assembly at the distal end of the endoscopic instrument;

a flexible member connected to and extending from the end effector assembly; and a handle assembly including a handle member having an inner bore, a hollow nose member having a shank configured for insertion into the inner bore, and a biasing element within the inner bore for biasing the flexible member relative to the handle member, wherein the flexible member is inserted into the hollow nose member and connected to the handle assembly and wherein the biasing element is an integrally formed portion of the flexible member.

12. An endoscopic instrument having a proximal end and a distal end, the endoscopic instrument comprising:

an end effector assembly at the distal end of the endoscopic instrument;

a flexible member connected to and extending from the end effector assembly; and a handle assembly including a handle member having an inner bore, a hollow nose member having a shank configured for insertion into the inner bore, and a biasing element within the inner bore for biasing the flexible member relative to the handle member, wherein the flexible member is inserted into the hollow nose member and connected to the handle assembly and wherein the nose member includes a strain relief element extending distally from the distal end of the nose member, said strain relief element being integrally molded to the nose member.

13. A conduit and handle assembly for use with a surgical instrument, the assembly comprising:

a flexible conduit, having a longitudinal axis defining a longitudinal direction;

a handle member having an inner bore;

a hollow nose member having a shank configured for insertion into the inner bore and for receiving the flexible conduit; and a biasing element within the inner bore, the biasing element configured for biasing the flexible conduit in the longitudinal direction relative to the handle member; and a retaining element integrally formed from the flexible conduit and configured for a retention between the handle member and the nose member.

14. A conduit and handle assemble for use with a surgical instrument, the assembly comprising:

a flexible conduit, having a longitudinal axis defining a longitudinal direction;

a handle member having an inner bore;

a hollow nose member having a shank configured for insertion into the inner bore and for receiving the flexible conduit; and a biasing element within the inner bore, the biasing element being an integrally formed portion of the nose member and configured for biasing the flexible conduit in the longitudinal direction relative to the handle member.

15. The assembly of claim 14, wherein the biasing element is compressible.

16. The assembly of claim 14, wherein the biasing element is located on the shank.

17. The assemble of claim 16, wherein the biasing element includes a plurality of rings integrally molded into the shank, the rings stacked with offset supports therebetween and capable of out-of-plane bending.

18. The assembly of claim 14, wherein the biasing element includes a leaf spring.

19. A conduit and handle assembly for use with a surgical instrument, the assembly comprising:

a flexible conduit, having a longitudinal axis defining a longitudinal direction;

a handle member having an inner bore;

a hollow nose member having a shank configured for insertion into the inner bore and for receiving the flexible conduit; and a biasing element within the inner bore, the biasing element being an elastomeric ring formed as an element separate from the nose member and configured for biasing the flexible conduit in the longitudinal direction relative to the handle member.

20. A conduit and handle assembly for use with a surgical instrument, the assembly comprising:

a flexible conduit, having a longitudinal axis defining a longitudinal direction;

a handle member having an inner bore;

a hollow nose member having a shank configured for insertion into the inner bore and for receiving the flexible conduit; and a biasing element within the inner bore, the biasing element being formed as an element separate from the nose member and configured for biasing the flexible conduit in the longitudinal direction relative to the handle member, the biasing element being located between a retaining element configured for affixation to a proximal end of the flexible conduit and the nose member.

21. A conduit and handle assembly for use with a surgical instrument, the assembly comprising:

a flexible conduit, having a longitudinal axis defining a longitudinal direction;

a handle member having an inner bore;

a hollow nose member having a shank configured for insertion into the inner bore and for receiving the flexible conduit; and a biasing element within the inner bore, the biasing element configured for biasing the flexible conduit in the longitudinal direction relative to the handle member, wherein the biasing element is an integrally formed portion of the flexible conduit.

22. An endoscopic instrument having a proximal end and a distal end, the endoscopic instrument comprising:

an end effector assemble at the distal end of the endoscopic instrument;

a flexible member, having a longitudinal axis defining a longitudinal direction, connected to and extending from the end effector assembly; and a handle assembly including a handle member having an inner bore, a hollow nose member having a shank configured for insertion into the inner bore, and a biasing element within the inner bore configured for biasing the flexible member in the longitudinal direction relative to the handle member, wherein the flexible member is inserted into the hollow nose member and connected to the handle assembly and wherein the biasing element is an integrally formed portion of the nose member.

23. The endoscopic instrument of claim 22, wherein the biasing element is compressible.

24. The endoscopic instrument of claim 22, wherein the biasing element is located on the shank.

25. The endoscopic instrument of claim 24, wherein the biasing element includes a leaf spring.

26. The endoscopic instrument of claim 24, wherein the biasing element includes a plurality of rings integrally molded into the shank, the rings stacked with offset supports therebetween and capable of out-of-plane bending.

27. An endoscopic instrument having a proximal end and a distal end, the endoscopic instrument comprising:

an end effector assembly at the distal end of the endoscopic instrument;

a flexible member, having a longitudinal asix defining a longitudinal direction, connected to and extending from the end effector assembly; and a handle assembly including a handle member having an inner bore, a hollow nose member having a shank configured for insertion into the inner bore, and a biasing element within the inner bore configured for biasing the flexible member in the longitudinal direction relative to the handle member, wherein the flexible member is inserted into the hollow nose member and connected to the handle assembly and wherein the biasing element is an elastomeric ring formed as an element separate from the nose member.

28. An endoscopic instrument having a proximal end and a distal end, the endoscopic instrument comprising:

an end effector assembly at the distal end of the endoscopic instrument;

a flexible member, having a longitudinal asix defining a longitudinal direction, connected to and extending from the end effector assembly; and a handle assembly including a handle member having an inner bore, a hollow nose member having a shank configured for insertion into the inner bore, and a biasing element within the inner bore configured for biasing the flexible member in the longitudinal direction relative to the handle member, wherein the flexible member is inserted into the hollow nose member and connected to the handle assembly and wherein the biasing element is formed as an element separate from the nose member and is located between a retaining element affixed to a proximal end of the flexible member and the nose member.

29. An endoscopic instrument having a proximal end and a distal end, the endoscopic instrument comprising:

an end effector assembly at the distal end of the endoscopic instrument;

a flexible member, having a longitudinal axis defining a longitudinal direction, connected to and extending from the end effector assembly; and a handle assembly including a handle member having an inner bore, a hollow nose member having a shank configured for insertion into the inner bore, and a biasing element within the inner bore configured for biasing the flexible member in the longitudinal direction relative to the handle member, wherein the flexible member is inserted into the hollow nose member and connected to the handle assembly and wherein the biasing element is an integrally formed portion of the flexible member.

30. An endoscopic instrument having a proximal end and a distal end, the endoscopic instrument comprising:

an end effector assembly at the distal end of the endoscopic instrument;

a flexible member having a longitudinal axis defining a longitudinal direction, connected to and extending from the end effector assembly; and a handle assembly including a handle member having an inner bore, a hollow nose member having a shank configured for insertion into the inner bore, and a biasing element within the inner bore configured for biasing the flexible member in the longitudinal direction relative to the handle member, wherein the flexible member is inserted into the hollow nose member and connected to the handle assembly and wherein the nose member includes a strain relief element integrally molded to the nose member and extending distally form the distal end of the nose member.

31. A conduit and handle assembly for use with a surgical instrument, the assembly comprising:

a flexible conduit, having a longitudinal axis defining a longitudinal direction;

a handle member having an inner bore;

a hollow nose member having a shank configured for insertion into the inner bore and for receiving the flexible conduit; and a biasing element within the inner bore, the biasing element configured for biasing the flexible conduit in the longitudinal direction relative to the handle member, wherein the biasing element includes at least one ring with supports on a first side and a second side of the ring, the supports coupling the ring to the shank, the supports on the first side of the ring being circumferentially offset from the supports on the second side of the ring.

* * * * *

UNITED STATES PATENT AND TRADEMARK OFFICE

CERTIFICATE OF CORRECTION

PATENT NO. : 6,273,882 B1
DATED : August 14, 2001
INVENTOR(S) : Whittier et al.

It is certified that error appears in the above-identified patent and that said Letters Patent is hereby corrected as shown below:

Column 12, claim 1,
Line 9, after "having an", delete the comma.
Line 21, "arrays" should read -- arms --.

Column 12, claim 4,
Line 53, "bore ard" should read -- bore and --.

Column 12, claim 4,
Line 59, "ring" should read -- rings --.
Line 60, "aid" should read -- and --.

Column 13, claim 8,
Line 34, "insenion" should read -- insertion --.

Column 13, claim 9,
Line 50, "aid" should read -- and --.

Column 14, claim 13,
Line 58, before "retention", delete "a".

Column 14, claim 14,
Line 60, "assemble" should read -- assembly --.

Column 15, claim 17,
Line 10, "assemble" should read -- assembly --.

Column 15, claim 22,
Line 10, "assemble" should read -- assembly --.

Column 16, claim 27,
Line 23, "asix" should read -- axis --.

Column 16, claim 28,
Line 41, "asix" should read -- axis --.

Column 17, claim 30,
Line 10, after "a flexible member", insert a comma.

UNITED STATES PATENT AND TRADEMARK OFFICE

CERTIFICATE OF CORRECTION

PATENT NO. : 6,273,882 B1
DATED : August 14, 2001
INVENTOR(S) : Whittier et al.

It is certified that error appears in the above-identified patent and that said Letters Patent is hereby corrected as shown below:

Column 18, claim 30,
Line 1, "form" should read -- from -

Signed and Sealed this

Sixteenth Day of April, 2002

*Attest:*

JAMES E. ROGAN

*Attesting Officer* *Director of the United States Patent and Trademark Office*